US00PP12375P2

(12) United States Plant Patent

Werner et al.

(10) Patent No.: US PP12,375 P2

(45) Date of Patent: Jan. 29, 2002

(54) PEACH-CHALLENGER CULTIVAR

(76) Inventors: Dennis James Werner, 268 Kilgore Hall, Horticultural Science Department, North Carolina State University; Steve Martin Worthington; Layne Karlton Snelling, both of 59 Kilgore Hall, Horticultural Science Department, North Carolina State University, all of Raleigh, NC (US) 27695-7609

( * ) Notice: Subject to any disclaimer, the term of this patent is extended or adjusted under 35 U.S.C. 154(b) by 0 days.

(21) Appl. No.: 09/233,140

(22) Filed: Jan. 19, 1999

(51) Int. Cl.[7] ..... A01H 5/00

(52) U.S. Cl. ..... Plt./194

(58) Field of Search ..... Plt./194

(56) References Cited

U.S. PATENT DOCUMENTS

PP11,017 P * 7/1999 Chamberlin ..... Plt./198

* cited by examiner

*Primary Examiner*—Bruce R. Campell
*Assistant Examiner*—Anne Marie Grünberg

(57) ABSTRACT

A new and distinct variety of peach tree which is distinguished by the ability of its flower buds to survive cold temperatures that are typically injurious to flower buds of standard peach varieties during dormancy and bloom, resulting in the production of fruit even in years when such cold temperatures eliminate the crop on standard peach varieties. The variety produces freestone, yellow flesh fruit that are mature for fresh consumption approximately July 1 in south central North Carolina.

6 Drawing Sheets

SUMMARY OF THE INVENTION

The new and distinct variety of peach [*Prunus persica* (L.) Batsch] originated from a cross of 'Redhaven'× (NCA001, NCA002, and NCA003 bulk) made in 1987 at the Sandhills Research Station at Jackson Springs, N.C. NCA001, NCA002, and NCA003 all originated from the 1981 cross of 'Reliance'×'Biscoe'. 'Biscoe' was released and named as a peach variety by the North Carolina Agricultural Research Service in 1968. 'Reliance' was released by the University of New Hampshire in 1964, and 'Redhaven' was released by Michigan State University in 1940. None of these three varieties are patented, and all are currently available in commerce.

Plants and fruit of this new variety differ phenotypically from its parents. The new variety produces medium, yellow flesh, firm fruit that ripen in early July in North Carolina, about 1 week after 'Redhaven' and 'Reliance', and 3.5 weeks before 'Biscoe'. The round, smooth fruit have attractive red skin color, the foliage and fruit have high bacterial spot resistance, and the flower buds, flowers and young fruit exhibit high resistance to freezing temperatures. The new variety differs from 'Reliance' in having more attractive fruit skin color, firmer flesh, improved flesh texture, and larger fruit. The new variety differs from 'Redhaven' in having higher resistance of the flower buds to freezing temperatures, and greater resistance to bacterial spot disease.

The approximately 300 seeds resulting from this controlled hybridization were germinated in a greenhouse at North Carolina State University, Raleigh, N.C. in the fall of 1987 and planted in the field in spring of 1988. These trees first produced fruit in 1990, and one seedling, designated NC-C3-68, was selected for its medium, yellow flesh fruit, attractive red color, bacterial spot resistance, low acid fruit, and heavy fruit production.

During 1993 and 1994, the original plant selection was propagated asexually by grafting of vegetative buds onto the standard peach rootstock 'Lovell', at the Sandhills Research Station. 'Lovell' is unpatented and is currently available in commerce. Two grafted trees of the variety were established in test plots at Sandhills Research Station in 1994, and twelve grafted trees of the variety were established at the same station in 1998.

The new variety has routinely been asexually multiplied by grafting, specifically 'T' budding. It readily forms a graft union with peach rootstock and resumes normal growth. During all asexual propagation, the characteristics of the original plant have been maintained and no aberrant phenotypes have appeared.

Test plantings and performance evaluation over seven years at the Sandhills Research Station demonstrate this variety to be consistent in its characteristics, taking into consideration the normal variation in time of flowering and time of ripening associated with yearly climatic variation.

Plants of the new variety are very vigorous and grow rapidly after establishment of trees in the field. Young trees have averaged 2–3 feet of growth per year. Plants are semi-upright in growth habit. Angles between the trunk and main branches average 70 degrees. Flowering sometimes occurs in the second year of growth, but more commonly trees begin flowering in the third year after establishment. Flowers are single, medium pink, and in accordance with typical classification of peach flowers by nurseries and professionals, are classified as non-showy. Flowering usually begins in mid March in Raleigh, N.C.; the chilling requirement is estimated to be 950 hours below 4 C., based on comparison of flowering time to standard varieties.

Fertility of flowers is excellent, and fruit set is generally very high in most years. Flowers are self-fertile. Flowers have shown excellent resistance to cold temperatures during winter dormancy and during flower development in the spring. Trees produced 20% of a full fruit crop in 1996, a year in which all commercial varieties in research plots failed to produce a fruit crop at the Sandhills Research Station because of low temperature injury. In that year, trees in flower were exposed to six consecutive nights of below freezing temperatures from March 9 through March 14, inclusive. Fruit are medium to large, averaging 6.35 cm, yellow fleshed, and show normal acidity typical of peach. Fruit ripen in late June to early July in Jackson Springs, N.C., averaging July 1 over 5 years of observation. Resistance of foliage to bacterial spot disease is excellent. Bacterial spot resistance was assessed over three years of observation in field plots at the Sandhills Research Station, Jackson Springs, N.C. by rating trees for leaf defoliation after natural field infection.

The new variety has been named the CHALLENGER cultivar.

BRIEF DESCRIPTION OF THE PHOTOGRAPH

The accompanying photographs shows typical specimens of the cultivar in color as nearly true as it is reasonably possible to make in a color illustration of these characters.

DETAILED DESCRIPTION OF THE NEW VARIETY

Figure 1:
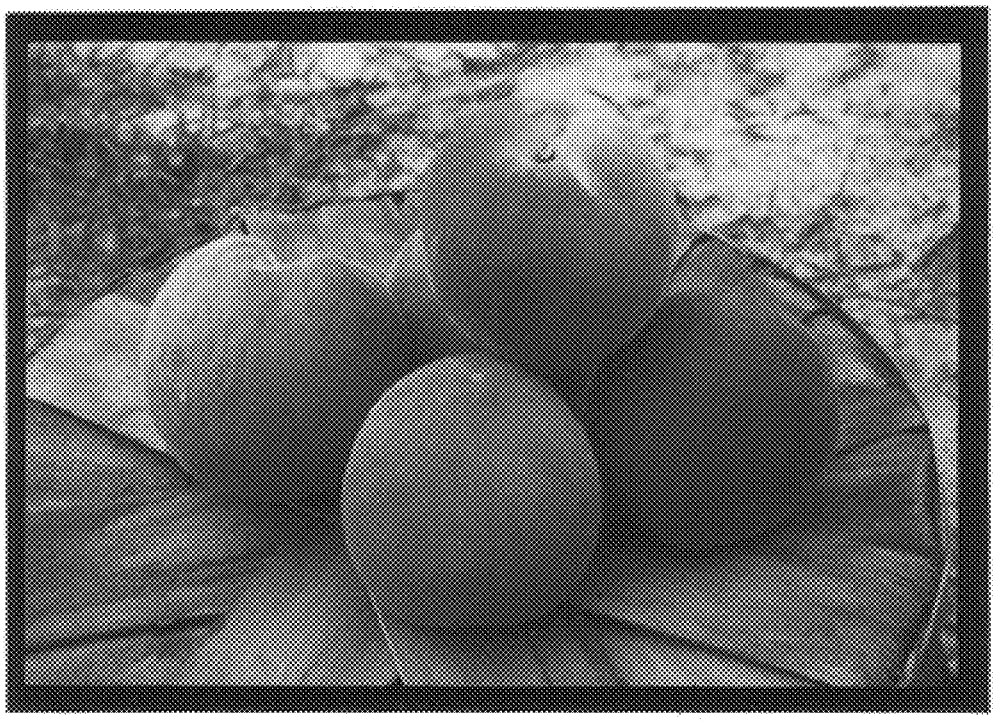
FIG. 1 shows mature fruit of 'Challenger' on the tree showing the bright red skin overcolor and bright yellow ground color.
Figure 2:
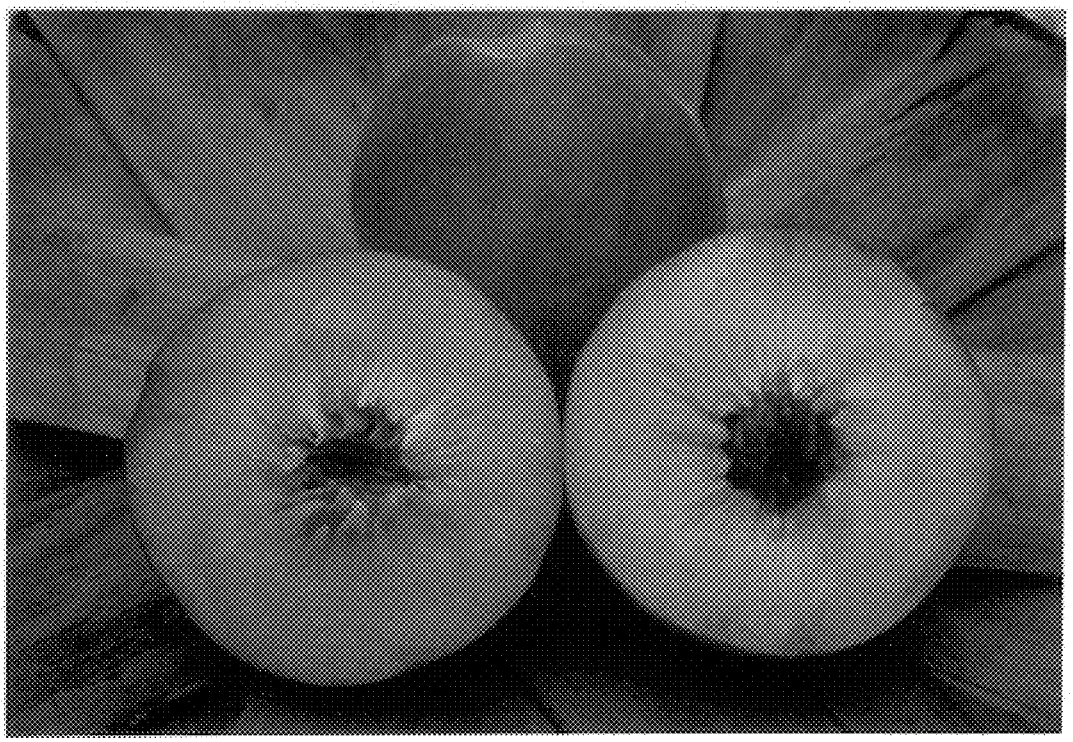
FIG. 2 shows a cross section of a cut, mature fruit showing the orange-yellow flesh color, stone, and pit cavity.
Figure 3:
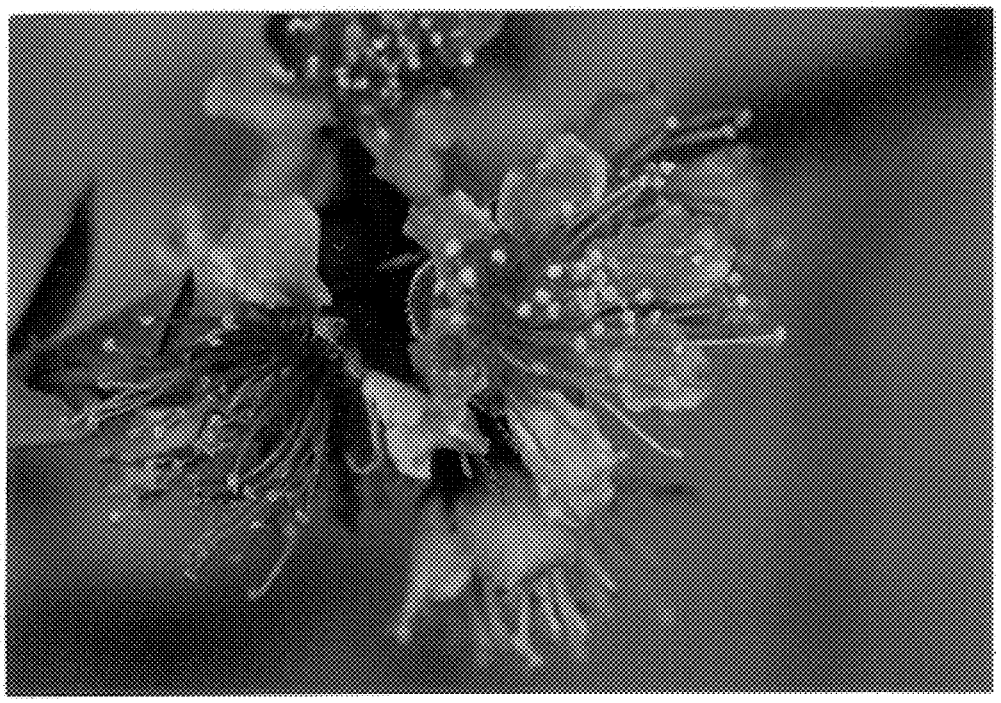
FIG. 3 shows a close up of the flower of 'Challenger', showing the color and characteristics of the petals, stamens, and pistil.
Figure 4:
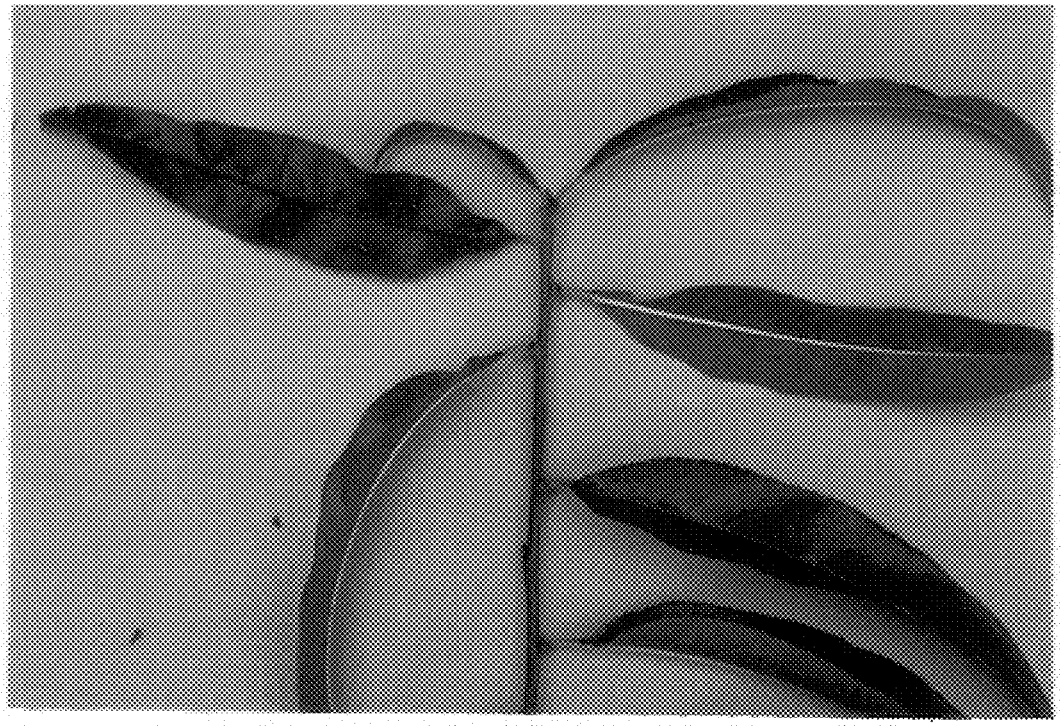
FIG. 4 shows the upper and lower surfaces of mature leaves of 'Challenger'.
Figure 5:
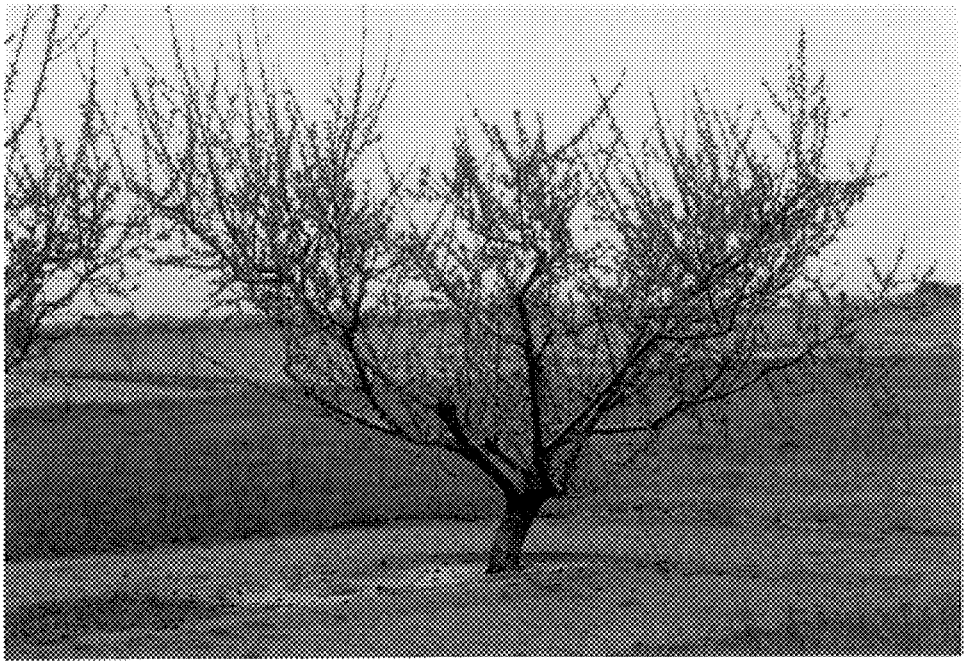
FIG. 5 shows a mature seven-year-old tree of 'Challenger', showing typical tree size and form.
Figure 6:
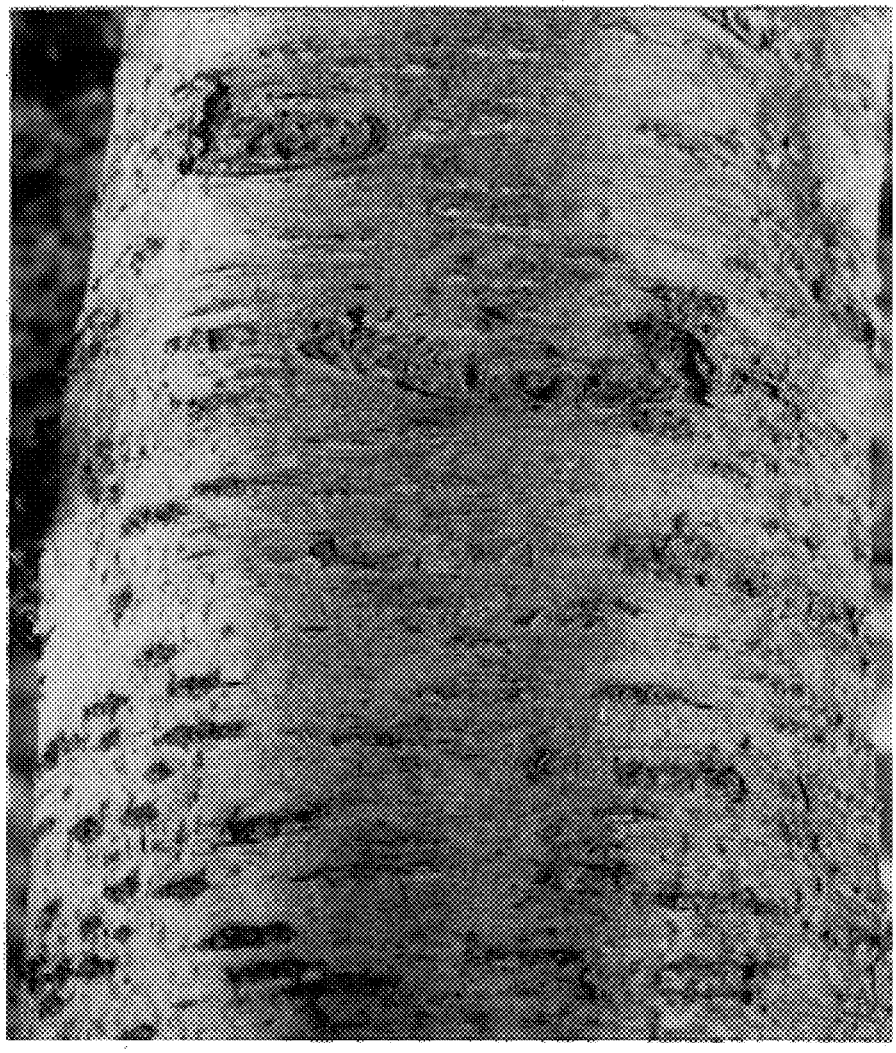
FIG. 6 shows a close up of the trunk of a seven-year-old tree of 'Challenger', showing the bark color and texture.

The following is a detailed description of the botanical and pomological characteristics of the subject peach. Color data are presented in Royal Horticultural Society Colour chart designations. Where dimensions, sizes, colors and other characteristics are given, it is to be understood that such characteristics are approximations of averages set forth as accurately as practicable.

The descriptions reported herein are from seven-year-old specimens grown at Jackson Springs, N.C. unless otherwise noted.

Tree:

*Size.*—Large. Height=9 feet. Breadth=16 feet.
*Vigor.*—Very vigorous.
*Growth.*—Semi-upright. Main branch angle 70 degrees.
*Production.*—High. Average 3.4 bushels of fruit per mature tree.

Trunk:

*Size.*—Circumference=19 inches (measured 12 inches above soil).
*Texture.*—Normal for peach tree bark.
*Color.*—Greyed-green 197D.

Branches:

*Size.*—Main scaffold branch circumference=11.25 inches.
*Surface.*—Smooth (new) to medium rough (old).
*Lenticels.*—Quantity=82 per inch of shoot on two-year-old wood. Color of lenticel=orange-white 159B.
*Color.*—Greyed-orange 175B (new growth — upper surface), yellow-green 146C (new growth — lower surface), to greyed-green 197B (two-year-old shoot — upper surface). Moderate red color (45A) on upper surface of new growth.

Foliage:

*Leaves.*—Large. Mature leaf length 14.8 cm; width 3.2 cm.
*Form.*—Lanceolate. Acutely pointed.
*Thickness.*—Medium.
*Texture.*—Smooth to slightly rugose.
*Margin.*—Crenate.
*Petiole.*—Length=0.83 cm. Width=0.14 cm. Color=yellow-green (145B).
*Glands.*—Located on base of leaf and upper portion of petiole. Shape=reniform. Average number=2.25 per leaf. Color=yellow-green (145B).
*Color.*—Mature leaf upper surface — yellow green (147A). Mature leaf lower surface — yellow green (148A).

Flower buds:

*Size.*—Length=0.397 cm. Diameter=0.283 cm.
*Shape.*—Slightly elongate.
*Color of bud scales.*—Greyed-green (197B).

Flowers:

*Date of first bloom.*—March 10 to March 30 in Jackson Springs, N.C. Varies yearly due to weather conditions.
*Petal size.*—Length=1.0 cm. Width=0.7 cm.
*Petal shape.*—Slightly elongated.
*Bloom diameter*—2.70 cm.
*Fragrance.*—None.
*Lastingness of bloom.*—7 to 10 days, influenced greatly by weather.
*Petal color.*—Red-purple (63C).
*Calyx color.*—Grayed-purple (183D).
*Reproductive organs.*—Stamens — erect, numerous (average number=27). Anther color=greyed-red (179A). Filament color=white (155C). Pistils — usually one. Color=greyed yellow (160-B). Pollen — normal and abundant. Color=yellow-orange (14B).
*Fertility.*—Self-fertile.
*Number of flowers per bud.*—One.
*Number of petals per flower.*—Average 5.
*Sepal color.*—Greyed-red (181B).

Fruit:

*Maturity.*—Early to mid-season. Late June to early July. Average July 1.
*Size.*—Medium to large. Average 6.4 cm diameter.
*Form.*—Round.
*Suture.*—Shallow to slightly grooved.
*Pubescence.*—Light.
*Pedicel color at fruit maturity.*—Yellow-green (144B).
*Pedicel size.*—Length=4 mm. Width=2 mm.
*Skin.*—Color=70–80% red overcolor (45A) with yellow ground color (18A). No tendency to crack. Skin tenacious to flesh.
*Flesh color.*—Yellow-orange (21B), with little red intrusion (45A).
*Flesh fiber.*—None.
*Flesh texture.*—Smooth.
*Flesh acidity* (*pH — ripe fruit*).—3.9.
*Eating quality.*—Excellent.
*Sugar content.*—14.2 Brix.
*Uses.*—Fresh consumption.
*Stone.*—Freestone, Shape=ovoid. Color=greyed-orange (165A). Texture=rough. Length=1.3 inches.

Width=0.79 inches. Thickness=0.61 inches. Tendency to split=none.

*Surface of pit cavity.*—Rough, yellow-orange (15C).

The variety: The most distinctive features of the variety are its high quality yellow flesh fruit, its late flowering (high chilling requirement), very high resistance of flower buds and flowers to cold temperature injury, and its high resistance to bacterial spot disease.

We claim:

1. A new and distinct variety of edible peach, substantially as illustrated and described, characterized by high quality yellow flesh fruit, its late flowering, its high resistance of flower buds and flowers to cold temperatures, and its high resistance to bacterial spot disease.

* * * * *